United States Patent [19]

Guilbeaux

[11] Patent Number: 4,929,644

[45] Date of Patent: May 29, 1990

[54] THICKENED ORGANIC COMPOSITION HAVING BIOCIDAL ACTIVITY AND AN ADDITIVE FOR THICKENING AND IMPARTING BIOCIDAL ACTIVITY TO AN ORGANIC COMPOSITION

[75] Inventor: Ronald D. Guilbeaux, New Hope, Pa.

[73] Assignee: Rheox, Inc., Hightstown, N.J.

[21] Appl. No.: 923,106

[22] Filed: Oct. 24, 1986

[51] Int. Cl.$^5$ .............................................. A61K 31/14
[52] U.S. Cl. ..................................... 514/642; 514/643
[58] Field of Search ................................ 514/642, 643

[56] References Cited

U.S. PATENT DOCUMENTS

| | | | |
|---|---|---|---|
| 2,033,856 | 3/1936 | Smith | 546/10 |
| 2,355,356 | 8/1944 | Young | 564/490 |
| 2,531,427 | 11/1950 | Hauser | 556/9 |
| 2,531,440 | 11/1950 | Jordan | 252/49.7 |
| 2,548,679 | 4/1951 | Olin | 564/285 |
| 2,658,869 | 11/1953 | Stross et al. | 252/28 |
| 2,677,661 | 5/1954 | O'Halloran | 252/49.6 |
| 2,739,067 | 3/1956 | Ratcliffe | 106/30 |
| 2,750,296 | 6/1956 | Curado et al. | 106/30 |
| 2,754,219 | 7/1956 | Voet et al. | 106/32 |
| 2,767,177 | 10/1956 | Erickson | 544/64 |
| 2,775,617 | 12/1956 | Shapiro et al. | 564/296 |
| 2,859,234 | 11/1958 | Clem | 44/7.6 |
| 2,885,360 | 5/1959 | Haden et al. | 252/316 |
| 2,966,506 | 12/1960 | Jordan | 556/173 |
| 3,136,819 | 6/1964 | Shapiro et al. | 564/473 |
| 3,461,163 | 8/1969 | Boothe | 564/296 |
| 3,472,740 | 10/1969 | Boothe | 203/37 |
| 3,537,994 | 11/1970 | House | 252/13 |
| 3,929,849 | 12/1975 | Oswald | 260/448 C |
| 3,945,836 | 3/1976 | Miyata | 106/22 |
| 3,974,125 | 8/1976 | Oswald et al. | 260/40 R |
| 4,054,537 | 10/1977 | Wright et al. | 252/316 |
| 4,081,496 | 3/1978 | Finlayson | 260/864 |
| 4,097,437 | 6/1978 | Dhake | 260/29.4 R |
| 4,105,578 | 8/1978 | Finlayson et al. | 252/316 |
| 4,116,866 | 9/1978 | Finlayson | 252/316 |
| 4,193,806 | 3/1980 | Finlayson | 106/20 |
| 4,208,218 | 6/1980 | Finlayson | 252/316 |
| 4,216,135 | 8/1980 | Finlayson | 252/316 |
| 4,287,086 | 9/1981 | Finlayson et al. | 252/316 |
| 4,317,737 | 3/1982 | Oswald et al. | 252/28 |
| 4,391,637 | 7/1983 | Mardis et al. | 106/20 |
| 4,410,364 | 10/1983 | Finlayson et al. | 252/315.2 |
| 4,412,018 | 10/1983 | Finlayson et al. | 252/315.2 |
| 4,434,075 | 2/1984 | Mardis et al. | 252/315.2 |
| 4,434,076 | 2/1984 | Mardis et al. | 252/315.2 |
| 4,450,095 | 5/1984 | Finlayson | 252/315.2 |
| 4,517,112 | 5/1985 | Mardis et al. | 252/315.2 |
| 4,631,091 | 12/1986 | Goodman | 106/308 N |
| 4,659,571 | 4/1987 | Laba | 514/643 |
| 4,664,820 | 5/1987 | Magauran et al. | 252/28 |
| 4,683,259 | 7/1987 | Goodman | 524/447 |

FOREIGN PATENT DOCUMENTS 1106281 3/1968 United Kingdom .
1592271 7/1981 United Kingdom .

*Primary Examiner*—Allen J. Robinson
*Attorney, Agent, or Firm*—Burns, Doane, Swecker & Mathis

[57] ABSTRACT

A thickened organic composition containing a first organophilic clay which will increase the viscosity of the composition and a second organophilic clay which is different from the first and which will impart biocidal activity to the composition. The second organophilic clay is the reaction product of a smectite-type clay and an organic cation having a benzyl group and a long chain alkyl group. The first and second organophilic clays can be mixed into the organic composition as an additive and may be prepared by using a mixture of cations.

37 Claims, No Drawings

THICKENED ORGANIC COMPOSITION HAVING BIOCIDAL ACTIVITY AND AN ADDITIVE FOR THICKENING AND IMPARTING BIOCIDAL ACTIVITY TO AN ORGANIC COMPOSITION

BACKGROUND OF THE INVENTION

1. Field of the Invention

The present invention relates to a thickened organic composition and an additive which thickens and imparts biocidal activity to an organic composition.

2. Description of the Prior Art

Organophilic clays are well-known and are used to thicken a variety of organic compositions. Their usefulness is primarily directed to their ability to act as rheological agents. Thus, the organophilic clays are oftentimes used in topical preparations because of their rheological properties. One example of this utility is set forth in published U.K. application 2,096,891 wherein various- commercially available organophilic clays can be used to thicken an anhydrous antiperspirant composition.

Organophilic clays are also used in cosmetic formulations. However, since typical cosmetic formulations generally last several months and are opened frequently while coming in contact with human hands and the environment, cosmetics are exposed to a variety of microorganisms. Absent some type of biocide, these preparations could eventually introduce undesirable microorganisms onto the human skin, eyes or mucous membranes.

A number of biocidal compounds are known. In particular, it is known that certain quaternary compounds exhibit biocidal activity. In U.S. Patent No. 3,299,073, a vast number of quaternary ammonium compounds are disclosed. The compounds are described as being microbiologically active and are prepared by the reaction of certain quaternary ammonium hydroxides or their salts of inorganic acids with aromatic amino sulfonic acids or their salts and substituted aromatic amino sulfonic acids containing a defined anionic group attached to the aromatic nucleus. Exemplary quaternary ammonium compounds include alkyldimethyl benzyl ammonium chlorides. A number of suggested uses are presented including imparting laundry-resistant antimicrobial characteristics to textiles.

Additional types of quaternary compounds having biocidal properties are described in U.S. Patent No. 3,361,793. These water-insoluble, microbiologically active compounds are prepared by the reaction of certain quaternary ammonium hydroxides or their water-soluble salt with aromatic di- or poly-carboxylic acids or their water-soluble salts. An exemplary group of compounds include alkyl dimethyl benzyl ammonium chloride in which the alkyl group has from 8 to 22 carbon atoms. These compounds were found to exhibit high microbiological activity despite their relative insolubility in water. Also see U.S. Patent No. 3,361,794. Once again, the primary area of utility is in the area of textiles.

A bacteriostatic or germicidal paper or tissue is disclosed in U.S. Patent No. 3,227,614. The tissue or paper is contacted with a non-aqueous vehicle containing a germicidal and bacteriostatic agent. The agent may be selected from a variety of quaternary ammonium compounds exemplified by alkyl ($C_8$–$C_{18}$) dimethyl benzyl ammonium chlorides.

U.S. Pat. No. 3,594,468 discloses a three-component spermicidal and germicidal composition wherein the third component is coco-benzyl-dimethyl ammonium halide.

Heretofore, the prior art has not recognized the benefit of nor suggested developing an organic composition which can be thickened using at least one organophilic clay and which can be imparted with biocidal activity using at least one different organophilic clay which itself may have rheological properties. The art has also not heretofore developed an additive which achieves the aforementioned benefits.

OBJECTS AND SUMMARY OF THE INVENTION

It is accordingly a general object of the present invention to provide a thickened organic composition having biocidal activity.

It is a further object of the present invention to provide a single organophilic composition which will increase the viscosity of an organic composition and which will also impart biocidal activity to the organic composition.

It is a still further object of the present invention to provide an organophilic composition containing a first organophilic clay which will increase the viscosity of the organic composition and a second organophilic clay which has biocidal activity.

It is a more specific object of the present invention to provide a topical, preferably a cosmetic formulation containing a first organophilic clay which will increase the viscosity of the organic composition and a second organophilic clay which has biocidal activity.

It is a further object of the present invention to provide an additive comprising a first organophilic clay which will increase the viscosity of an organic composition and a second organophilic clay which has biocidal activity. In one aspect, the present invention provides a thickened organic composition having biocidal activity. The composition comprises:

(a) an organic liquid;

(b) a first organophilic clay which will increase the viscosity of the organic liquid; and (c) a second organophilic clay which is different from the first organophilic clay and which has biocidal activity, said second organophilic clay being the reaction product of (i) a smectite-type clay having a cation exchange capacity of at least about 75 milliequivalents per 100 grams of clay, 100% active basis, and (ii) an organic cation having the following formula

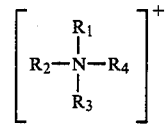

wherein $R_1$ is benzyl; $R_2$ is linear or branched, saturated or unsaturated alkyl group having 8 to 22 carbon atoms; and $R_3$ and $R_4$ are selected from (a) linear or branched alkyl groups having 1 to 22 carbon atoms; (b) aralkyl groups which are benzyl and substituted benzyl moieties including fused ring moieties having linear or branched 1 to 22 carbon atoms in the alkyl portion of the structure; (c) aryl groups such as phenyl and substituted phenyl including fused ring aromatic substituents;

(d) beta, gamma, unsaturated groups having 6 or less carbon atoms or hydroxyalkyl groups having 2 to 6 carbon atoms; and (e) hydrogen.

In another aspect, the present invention provides an additive for thickening and imparting biocidal activity to an organic composition. The additive comprises:

(a) a first organophilic clay which will increase the viscosity of the organic composition; and (b) a second organophilic clay which is different from the first organophilic clay and which has biocidal activity, said second organophilic clay being the reaction product of (i) a smectite-type clay having a cation exchange capacity of at least about 75 milliequivalents per 100 grams of clay, 100% active basis, and (ii) an organic cation having the following formula

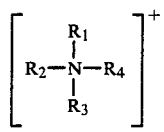

wherein $R_1$ is benzyl; $R_2$ is linear or branched, saturated or unsaturated alkyl group having 8 to 22 carbon atoms; and $R_3$ and $R_4$ are selected from (a) linear or branched alkyl groups having 1 to 22 carbon atoms; (b) aralkyl groups which are benzyl and substituted benzyl moieties including fused ring moieties having linear or branched 1 to 22 carbon atoms in the alkyl portion of the structure; (c) aryl groups such as phenyl and substituted phenyl including fused ring aromatic substituents; (d) beta, gamma, unsaturated groups having 6 or less carbon atoms or hydroxyalkyl groups having 2 to 6 carbon atoms; and (e) hydrogen.

Further advantages and features of the invention as well as the scope, nature and utilization of the invention will become apparent to those skilled in the art from the description of the preferred embodiments of the invention set forth below

DESCRIPTION OF THE PREFERRED EMBODIMENTS

As stated hereinabove, one aspect of the present invention relates to a thickened organic composition having biocidal activity which contains a first and a second organophilic clay. The organophilic clays used in certain aspects of the present invention may be selected from those organophilic clays well known in the art including those which are commercially available. In particular, the organophilic clays may be the reaction product of a smectite-type clay having a cation exchange capacity of at least about 75 milliequivalents per 100 grams of clay (100% active basis) and at least one quaternary ammonium compound having the definitions set forth below. Illustrative commercially available organophilic clays are illustrated by those available from NL Chemicals, Inc., of Hightstown, N.J. under the trademark "Bentone".

The smectite-type clays are well known in the art and are available from a variety of sources. The clays are preferably converted to the sodium form if they are not already in this form. This can conveniently be done by preparing an aqueous clay slurry and passing the slurry through a bed of cation exchange resin in the sodium form. Alternatively, the clay can be mixed with water and a soluble sodium compound such as sodium carbonate, sodium hydroxide, etc., and shearing the mixture such as with a pugmill or extruder.

Smectite clays prepared synthetically by either a pneumatolytic or, preferably, a hydrothermal synthesis process can also be used to prepare these novel organic clay complexes. Representative of such clays are the following:

Montmorillonite

where $0.55 \leq x \leq 1.10$, $f \leq 4$ and R is selected from the group consisting of Na, Li, NH$_4$, and mixtures thereof;

Bentonite

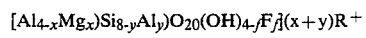

where $0 < x < 1.10$, $0 < y < 1.10$, $0.55 \leq (x+y) = 1.10$, $f \leq 4$ and R is selected from the group consisting of Na, Li, NH$_4$ and mixtures thereof;

Beidellite

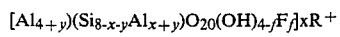

where $0.55 \leq x \leq 1.10$, $o \leq y \leq 0.44$, $f \leq 4$ and R is selected from the group consisting of Na, Li, NH$_4$, and mixtures thereof;

Hectorite

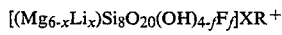

where $0.57 \leq x \leq 1.15$, $f \leq = 4$ and R is selected from the group consisting of Na, Li, NH$_4$, and mixtures thereof;

Saponite

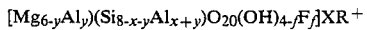

where $0.58 \leq x \leq 1.18$, $0 = \leq y \leq = 0.66$, $f=4$ and R is selected from the group consisting of Na, Li, NH$_4$, and mixtures thereof;

Stevensite

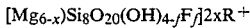

where $0.28 \leq x \leq 0.57$, $f=4$ and R is selected from the group consisting of Na, Li, NH$_4$, and mixtures thereof.

These clays may be synthesized hydrothermally by forming an aqueous reaction mixture in the form of a slurry containing mixed hydrous oxides or hydroxides of the desired metals with or without, as the case may be, sodium (or alternate exchangeable cation or mixture thereof) fluoride in the proportions defined by the above formulae and the preselected values of x, y and f for the particular synthetic smectite desired. The slurry is then placed in an autoclave and heated under autogenous pressure to a temperature within the range of approximately 100° to 325° C., preferably 275° to 300° C., for a sufficient period of time to form the desired product. Formulation times of 3 to 48 hours are typical at 300° C. depending on the particular smectite-type clay being synthesized. The optimum time can readily be determined by pilot trials. Representative hydrothermal processes for preparing synthetic smectite clays are described in U.S. Pat. Nos. 3,252,757, 3,586,478, 3,666,407, 3,671,190, 3,844,978, 3,844,979, 3,852,405 and 3,855,147, all of which are herein incorporated by reference.

The cation exchange capacity of the above-described clays can be determined by the well-known ammonium acetate method and is presented in milliequivalents (ME).

According to the present invention, the compound which is reacted with the smectite-type clay to obtain the organophilic clay with biocidal activity is a quaternary ammonium cation which has a benzyl group and one linear or branched, saturated or unsaturated alkyl group having 8 to 22 carbon atoms. The remaining two groups of the ammonium cation are chosen from (a) linear or branched alkyl groups having 1 to 22 carbon atoms; (b) aralkyl groups which are benzyl and substituted benzyl moieties including fused ring moieties having linear or branched 1 to 22 carbon atoms in the alkyl portion of the structure; (c) aryl groups such as phenyl and substituted phenyl including fused ring aromatic substituents; (d) beta, gamma, unsaturated groups having 6 or less carbon atoms or hydroxyalkyl groups having 2 to 6 carbon atoms; and (e) hydrogen.

The long chain alkyl radicals may be derived from natural occurring oils including various vegetable oils, such as corn oil, coconut oil, soybean oil, cottonseed oil, castor oil and the like, as well as various animal oils or fats such as tallow oil. The alkyl radicals may likewise be petrochemically derived such as from alpha olefins.

Representative examples of useful branched, saturated radicals include 12-methylstearyl; and 12-ethylstearyl. Representative examples of useful branched, unsaturated radicals include 12-methyloleyl and 12-ethyloleyl. Representative examples of unbranched saturated radicals include lauryl; stearyl; tridecyl; myristyl (tetradecyl); pentadecyl; hexadecyl; hydrogenated tallow, docosonyl. Representative examples of unbranched, unsaturated and unsubstituted radicals include oleyl, linoleyl, linolenyl, soya and tallow.

Additional examples of aralkyl, that is benzyl and substituted benzyl moieties would include those materials derived from, e.g., benzyl halides, benzhydryl halides, trityl halides, alpha-halo-alpha-phenylalkanes wherein the alkyl chain has from 1 to 22 carbon atoms such as 1-halo-1-phenylethane, 1-halo-1-phenylpropane, and 1-halo-1-phenyloctadecane; substituted benzyl moieties such as would be derived from ortho, meta and para-chlorobenzyl halides, para-methoxybenzyl halides, ortho, meta and para-nitrilobenzyl halides, and ortho, meta and para-alkylbenzyl halides wherein the alkyl chain contains from 1 to 22 carbon atoms; and fused ring benzyl-type moieties such as would be derived from 2-halomethylnaphthalene, 9-halomethylanthracene and 9-halomethylphenanthrene, wherein the halo group would be defined as chloro, bromo, iodo, or any other such group which serves as a leaving group in the nucleophilic attack of the benzyl type moiety such that the nucleophile replaces the leaving group on the benzyl type moiety.

Examples of aryl groups would include phenyl such as in N-alkyl and N,N-dialkyl anilines, wherein the alkyl groups contain between 1 and 22 carbon atoms; ortho, meta and paranitro phenyl, ortho meta and para-alkyl phenyl, wherein the alkyl group contains between 1 and 22 carbon atoms, 2-, 3-, and 4-halophenyl wherein the halo group is defined as chloro, bromo, or iodo, and 2-, 3-, and 4-carboxyphenyl and esters thereof, where the alcohol of the ester is derived from an alkyl alcohol, where in the alkyl group contains between 1 and 22 carbon atoms, aryl such as a phenol, or aralkyl such as benzyl alcohols; fused ring aryl moieties such as naphthalene, anthracene, and phenanthrene.

The beta, gamma-unsaturated alkyl group may be selected from a wide range of materials. These compounds may be cyclic or acyclic, unsubstituted or substituted with aliphatic radicals containing up to 3 carbon atoms such that the total number of aliphatic carbon in the beta, gamma-unsaturated radical is 6 or less. The beta, gamma-unsaturated alkyl radical may be substituted with an aromatic ring that likewise is conjugated with the unsaturation of the beta, gamma moiety or the beta, gamma-radical is substituted with both aliphatic radicals and aromatic rings.

Representative examples of cyclic beta, gamma-unsaturated alkyl groups include 2-cyclohexenyl and 2-cyclopentenyl. Representative examples of acyclic beta, gamma-unsaturated alkyl groups containing 6 or less carbon atoms include propargyl; allyl(2-propenyl); crotyl(2-butenyl); 2-pentenyl; 2-hexenyl; 3-methyl-2-butenyl; 3-methyl-2-pentenyl; 2,3-dimethyl-2-butenyl; 1,1-diethyl-2-propenyl; 1,2-dimethyl propenyl; 2,4-pentadienyl; and 2,4-hexadienyl. Representative examples of acyclic-aromatic substituted compounds include cinnamyl (3-phenyl-2-propenyl); 2-phenyl-2-propenyl; and 3-(4 methoxyphenyl)-2-propenyl. Representative examples of aromatic and aliphatic substituted materials include 3-phenyl-2-cyclohexenyl; 3-phenyl-2-cyclopentenyl; 1,1-dimethyl-3-phenyl-2-propenyl; 1,1,2-trimethyl-3-phenyl-2-propenyl;2,3-dimethyl-3-phenyl-2-propenyl; 3,3-dimethyl-2-phenyl-2-propenyl; and 3-phenyl-2-butenyl.

The hydroxyalkyl group is selected from a hydroxyl substituted aliphatic radical wherein the hydroxyl is not substituted at the carbon adjacent to the positively charged atom, and the group has from 2 to 6 aliphatic carbons. The alkyl group may be substituted with an aromatic ring independently from the 2 to 6 aliphatic carbons. Representative examples include 2-hydroxyethyl; 3-hydroxypropyl; 4-hydroxypentyl; 6-hydroxyhexyl; 2-hydroxypropyl; 2-hydroxybutyl; 2-hydroxypentyl; 2-hydroxyhexyl; 2-hydroxycyclohexyl; 3-hydroxycyclohexyl; 4-hydroxycyclohexyl; 2-hydroxycyclopentyl; 3-hydroxycyclopentyl; 2-methyl-2-hydroxypropyl; 1,1,2-trimethyl-2-hydroxypropyl; 2-phenyl-2-hydroxyethyl; 3-methyl-2-hydroxybutyl; and 5-hydroxy-2-pentenyl.

The quaternary ammonium compound can thus be considered as having the cation following formula:

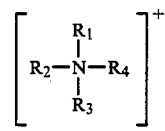

$$\left[\begin{array}{c} R_1 \\ | \\ R_2-N-R_4 \\ | \\ R_3 \end{array}\right]^+$$

wherein $R_1$ is a benzyl group, $R_2$ is a long chain alkyl group having 8 to 22 carbon atoms and $R_3$ and $R_4$ are representative of the other possible groups described above.

$R_1$ must always be benzyl which may contain substituents, such as alkyl, alkoxy, halo, etc., which do not substantially adversely affect the biocidal activity of the final reaction product. $R_2$ is preferably a linear or branched, saturated or unsaturated alkyl group having 12 to 22 carbon atoms. More preferably, $R_2$ is tallow, coco, soya, or the amino propyl amide of stearic acid and is most preferably coco or soya. $R_3$ and $R_4$ are preferably a lower alkyl containing 1 to 4 carbon atoms or a lower hydroxy alkyl containing 2 to 4 carbon atoms. More preferably, $R_3$ and $R_4$ are each methyl or hydroxyethyl.

Particularly preferred quaternary ammonium cations useful in preparing the organophilic clay with biocidal activity include dimethyl benzyl hydrogenated tallow ammonium, dihydroxyethyl benzyl coco ammonium, dihydroxyethyl benzyl tallow ammonium, dihydroxyethyl benzyl soya ammonium, dimethyl distilled C-20 benzyl ammonium, dimethyl benzyl amino propyl amide of stearic acid ammonium and dimethyl benzyl coco ammonium. Obviously, combinations of these ammonium compounds are envisioned in the practice of the present invention.

The organophilic clay which thickens the organic composition is different from organophilic clay having biocidal activity and is prepared by reacting a smectite-type clay (as previously defined) with an organic cation that is a quaternary ammonium cation having at least one linear or branched, saturated or unsaturated alkyl group having 8 to 22 carbon atoms, but with the proviso that the ammonium cation cannot have a benzyl group. More preferably, the organic cation has the following formula:

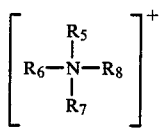

wherein $R_5$ is linear or branched, saturated or unsaturated alkyl group having 8 to 22 carbon atoms; and $R_6$, $R_7$ and $R_8$ are selected from (a) linear or branched alkyl groups having 1 to 22 carbon atoms; (b) aralkyl groups including fused ring moieties having linear or branched 1 to 22 carbon atoms in the alkyl portion of the structure; (c) aryl groups such as phenyl and substituted phenyl including fused ring aromatic substituents; (d) beta, gamma, unsaturated groups having 6 or less carbon atoms or hydroxyalkyl groups having 2 to 6 carbon atoms; and (e) hydrogen, with the proviso that none of $R_6$, $R_7$ or $R_8$ is benzyl. More preferably, $R_6$, $R_7$ and $R_8$ are selected from linear or branched alkyl groups having 1 to 22 carbon atoms and hydrogen with an exemplary preferred cation being dimethyl dihydrogenated tallow ammonium.

As is apparent from the above formula, mixtures of organophilic clays within the defined formula may also be used in accordance with the present invention.

A preferred quaternary ammonium cation contains two long-chain alkyl, especially hydrogenated tallow groups and a preferred specific quaternary ammonium cation is dimethyl dihydrogenated tallow ammonium. In its commonly available form, an organophilic clay prepared from this specific quaternary ammonium cation normally contains high microbial counts, generally in the range of 4,000 to 5,000 per gram of clay.

The concept behind employing the two defined organophilic clays involves combining one which will impart superior rheological properties to the organophilic clay with another which will impart excellent biocidal activity to the composition. Hence, the composition will not need other biocidal agents which can cause adverse (e.g., allergic) reactions especially if the composition is to be used topically. Advantageously, it has been discovered that the overall rheological properties of the organophilic clay will not be diminished and may even be enhanced by adding the organophilic clay with biocidal activity to the organic composition. Furthermore, by providing a combination of first organophilic clays and/or a combination of second organophilic clays, the thickening and biocidal activity can be tailored to the desired level for a given organic composition.

The amounts of the organic cations used to prepare the first and second organophilic clays depend on a variety of factors. Typical considerations include the type of smectite-type clay selected and the type of each of the quaternary ammonium cations selected. Thus, a sufficient amount or ratio of the quaternary ammonium cation should be used to achieve an organophilic clay with thickening and/or biocidal activity.

Generally, the amount of the quaternary ammonium cation reacted with the smectite-type clay (or the total amount of cations if a mixture is used) is from about 90 to about 150% of the cation exchange capacity of the smectite-type clay, preferably from about 96 to about 120% of the cation exchange capacity of the smectite-type clay. Thus, if the smectite-type clay is bentonite, which has a cation exchange capacity of about 95 milliequivalents per 100 grams of clay, 100% active basis, the amount of organic cation reacted will be from about 85 to about 143 milliequivalents, preferably from about 92 to about 115 milliequivalents per 100 grams of clay, 100% active basis.

The anion which will normally originally accompany the quaternary ammonium cation is typically one which will not adversely affect the reaction product or the recovery of the same. Such anions may be exemplified by chloride, bromide, iodide, hydroxyl, nitrite and acetate in amounts sufficient to neutralize the organic cation.

The preparation of the quaternary ammonium compound or salt (i.e., the organic cation paired with the anion) and the organophilic clay can be achieved by techniques well known in the art. For example, when preparing a quaternary ammonium salt, one skilled in the art would prepare a dialkyl secondary amine, for example, by the hydrogenation of nitriles, see U.S. Pat. No. 2,355,356, and then form the methyl dialkyl tertiary amine by reductive alkylation using formaldehyde as a source of the methyl radical. According to procedures set forth in U.S. Pat. No. 3,136,819 and U.S. Pat. No. 2,775,617, quaternary amine halide may then be formed by adding chloride or benzyl bromide to the tertiary amine. The contents of these three patents are hereby incorporated by reference. As is well known in the art, the reaction with benzyl chloride or benzyl bromide can be completed by adding a minor amount of methylene chloride to the reaction mixture so that a blend of products which are predominantly benzyl substituted is obtained. This blend may then be used without further separation of components to prepare the organophilic clay.

The organophilic clays can be prepared by admixing the clay, the quaternary ammonium compound and water together, preferably at a temperature within the range from about 20° to about 100° C., and preferably from about 35° to about 77° C. for a period of time sufficient for the organic compound to coat the clay particles. Thereafter, the organophilic clay can be subjected to a variety of optional recovery steps such as filtering, washing, drying and grinding.

One preferred way of preparing the first and second organophilic clays is to react a mixture of at least two organic cations with smectite-type clay so that the reaction product is partly formed of the organophilic clay which will thicken the organic composition and partly formed of the organophilic clay which will impart biocidal activity. Such a technique can simplify preparation of an additive which contains the first and second organophilic clays which, of course, includes mixtures of either or both of the first and second organophilic clays.

Illustrative of the numerous patents which describe quaternary ammonium compounds, their manner of preparation and their use in the preparation of organophilic clays are commonly assigned U.S. Pat. Nos. 2,966,506, 4,105,578, 4,116,866, 4,288,218, 4,391,637, 4,434,076 and 4,450,095, the contents of which are incorporated by reference.

The biocidal organophilic clay may be one component of a number of materials commonly applied to the skin surface. Exemplary topical compositions include cosmetic formulations, antiperspirant agents, deodorant agents, pigments, antifungal agents, insect repellents, and the like. The topical composition generally includes an organic liquid vehicle, such as vegetable oils, mineral oils, isopropyl myristate,. volatile silicones and may also contain conventional fillers and/or processing aids, such as lubricating agents. Of course, the specific ingredient or ingredients used in the topical formulations of the present invention are selected depending on the desired end use of the formulation.

As indicated earlier, the biocidal organophilic clay compositions of the present invention are especially effective in cosmetic formulations. The typical adjuvants used in formulating cosmetics are well-known to those in the cosmetics industry. Examples of cosmetic formulations include mascara, eye shadows, make-up compacts, make-up liquid, blushes or rouge, aftershave compositions, talcum powder compositions, antiseptic compositions, artistic chalk which may be applied anywhere on the skin surface and the like. Thus, liquid or solid formulations are well-suited to employ the organophilic clay which thickens the formulation and the organophilic clay which imparts biocidal activity to the formulation. Since each of the foregoing cosmetic formulations are generally intended for more than one application, the opportunity to attract bacteria or viruses is increased with use. Absent the presence of a biocide, the infecting organism could multiply within the cosmetic formulation and thereby cause skin, eye or mucous membrane irritation for the host.

The amounts of the organophilic clays added to the composition depends on various factors such as the nature of the composition, the specific organophilic clays and the desired degree of thickening and biocidal activity. In general, the amount of organophilic clay used to thicken the organic composition ranges from about 0.1 to about 10% by weight, preferably from about 1.0 to about 3.0% by weight of the total composition.

The organophilic clay which imparts biocidal activity to the composition is typically present in an amount ranging from about 0.03 to about 3.0% by weight, preferably from about 0.3 to about 0.9% by weight of the total composition. The amount of this organophilic clay is usually selected to obtain a microbial count in the composition of less than about 10, preferably less than about 2 and most preferably zero. Microbial count is determined by USP 18, FDA Microbial Limits using aerobic plate counts determined with trypticase soy agar and decimal dilutions which are incubated for 48 hours at 35OC. Polysorbate-20 is used for emulsification, suspension or neutralization.

The formulation may be prepared by mixing the organophilic clay which thickens the formulation, the organophilic clay which imparts biocidal activity and the other ingredients in any order. Of course, if the first and second organophilic clays are prepared together by using a mixture of cations, the preformed mixture of the first and second organophilic clays will be added as a single component. Mixing may be achieved in a conventional mixer, such as a V-blender, and is conducted for a period of time sufficient to ensure a substantially uniform mixture of the components.

Rather than measuring the amounts of organophilic clays separately and adding them either separately or in combination, the organophilic clay which will thicken the composition (which encompasses mixtures as indicated above) and the organophilic clay which will impart biocidal activity to the composition (which encompasses mixtures as indicated above) can be prepared in the form of an additive which can be added to the organic composition. The additive may also be prepared using the mixed cation technique discussed above.

As an additive, the organophilic clay which will thicken the organic composition is present in an amount ranging from about 3 to about 99% by weight, preferably from about 50 to about 90% by weight of the total amount of organophilic clay in the additive and the organophilic clay which will impart biocidal activity to the organic composition is present in an amount ranging from about 1 to about 97% by weight, preferably from about 10 to about 50% by weight of the total amount of organophilic clay in the additive.

Whether directly added to the organic composition or employed as an additive, the amounts of the first and second organophilic clays are preferably selected to obtain the benefits of each. That is, the amounts of the first and second organophilic clays are preferably selected such that the combination has a greater biocidal activity (as determined by microbial counts) than the same amount of the first organophilic clay and has a greater thickening efficiency than the same amount of the second organophilic clay.

Among the most common adjuvants in topical formulations include pigments which may be any of those known in the art which do not substantially adversely affect the desired characteristics of the formulation. Exemplary pigments are ultramarine blue, chromium oxide green, black iron oxides, titanium dioxides and mixtures thereof. When present, the amount of pigment is from about 0.2 to about 5.0%, preferably from about 0.5 to about 3.0% by weight.

An antifungal agent may also be present in the formulation in an amount ranging from about 0.5 to about 10.0%, preferably from about 1.0 to about 5.0% by weight. Exemplary antifungal agents include zinc undecylenate, undecylenic acid and mixtures thereof. The preferred antifungal agent is a mixture of zinc undecylenate and undecylenic acid.

Filler may be present in the formulation in order to dilute the concentration of the active ingredients or reduce the cost. Typical fillers include talc, dicalcium phosphate, hydrophobic starch, microcrystalline cellulose and mixtures thereof with the preferred filler being talc. When present, the amount of filler is from about 50 to about 99%, preferably from about 75 to about 90% by weight.

In the event that the formulation is a molded solid, a lubricating agent can be used in the formulation for the purpose of facilitating the release of the formulation from the compression mold. Typical lubricating agents include magnesium stearate, stearic acid, zinc stearate, calcium stearate and mixtures thereof with the preferred lubricating agent being magnesium stearate. When present, the amount of lubricating agent is from about 0.2 to about 2.0%, preferably from about 0.5 to about 1.0% by weight.

The following inventive examples and comparative examples are presented to illustrate and contrast the present invention. However, the examples should not be construed as limiting the invention. Unless otherwise indicated, all percentages are even in weight percent of the total formation.

EXAMPLE 1

The organophilic clay used is prepared according to standard techniques as described above. For the organic cation, varying proportions of cation A and cation B, as defined below, (originally added as the chloride salts) are used alone or in a mixture to yield various organophilic clays having the ability to thicken and impart biocidal properties.

A: Dimethyl Dihydrogenated Tallow Ammonium

B: Dihydroxyethyl Benzyl Hydrogenated Tallow Ammonium.

The resulting organophilic clay is processed and dried in the laboratory under normal processing conditions. The theoretical milliequivalent ratio (ME) of each of the quaternary ammonium cations is determined and listed in Table I as well as the actual milliequivalent ratio. To determine the biocidal effectiveness of each formulation, a count of the number of organisms in each gram of organophilic clay was conducted.

| Theoretical ME Ratio of A and B | | Actual ME Amount (per 100 g, 100% active basis | Microbial Count in Organisms/Gram |
|---|---|---|---|
| A | B | | |
| 100 | 0 | 99.0 | 5200 |
| 90 | 10 | 99.3 | 1100 |
| 80 | 20 | 98.5 | 140 |
| 70 | 30 | 103.2 | 80 |
| 60 | 40 | 105.7 | 40 |
| 50 | 50 | 114.2 | 0 |
| 40 | 60 | 114.0 | 0 |
| 30 | 70 | 112.2 | 0 |
| 20 | 80 | 120.9 | 0 |
| 10 | 90 | 120.6 | 0 |
| 0 | 100 | 119.2 | 0 |

The data in Table I demonstrates that the microbial count for the organophilic clay containing a dimethyl dihydrogenated tallow ammonium by itself is normally about 5,200, but in the presence of organophilic clay prepared from dihydroxyethyl benzyl tallow ammonium in a ratio of less than 50/50, it results in essentially zero microbial counts per gram of clay.

EXAMPLE 2

The organophilic clay is prepared in accordance with the procedure of Example 1 using organic cations C and D (originally added as the chloride salts) as defined below:

C: Dimethyl Dihydrogenated Tallow Ammonium

D: Benzyl Dimethyl Coco Ammonium (commercially available as the chloride salt from Humko Corporation)

In addition to determining the microbial count, an evaluation is also undertaken based on toluene gelling. Toluene gelling is used to analyze the efficiency of the organophilic clay. It is determined by mixing 2.0% by weight of the organophilic clay into toluene, thoroughly dispersing the organophilic clay and using a Brookfield Viscometer with a No. 3 spindle at 50 rpm. The data is presented in Table II.

TABLE II

| C/D ME Ratio | Total Organic Cation (ME per 100 g, 100% active basis) | 2.0% Org. Toluene Gels Brk. Vis., cps 50 rpm | Microbial Count Counts/Gram |
|---|---|---|---|
| 70/30 | 82.8 | 612 | 30 |
| 70/30 | 85.9 | 594 | — |
| 70/30 | 88.5 | 717 | 22 |
| 70/30 | 91.6 | 726 | <10 |
| 70/30 | 94.9 | 693 | <10 |
| 70/30 | 97.7 | 737 | <10 |
| 70/30 | 100.4 | 525 | <10 |
| 70/30 | 103.9 | 494 | <10 |
| 70/30 | 106.9 | 425 | <10 |
| 70/30 | 109.9 | 66 | <10 |
| 70/30 | 115.0 | 48 | <10 |
| 70/30 | 121.5 | 52 | <10 |
| 70/30 | 125.7 | 44 | <10 |
| 80/20 | 98.6 | 536 | 800 |
| 90/10 | 97.9 | 396 | 900 |
| 95/5 | 95.9 | 430 | 1400 |
| 100/0 | 98.4 | 349 | 1500 |
| 100/0 | 94.0 | 500 | — |

The data in Table II demonstrates that the microbial counts for an organophilic clay containing a dimethyl dihydrogenated tallow ammonium/benzyl dimethyl coco ammonium ratio of 70/30 at millequivalent ratios of 92 to 126 were all less than 10 counts per gram. The toluene gel viscosities were at least as good as, if not better than the viscosities obtained using only an organophilic clay prepared from only dimethyl dihydrogenated tallow ammonium chloride.

EXAMPLE 3

An organophilic clay is prepared using varying amounts of dimethyl dihydrogenated tallow ammonium chloride (A) as well as one of the following quaternary cations (in their chloride salt form) identified below such that the total amount of cation reacted is about 115 milliequivalents per 100 grams of clay, 100% active basis:

A: Dihydroxyethyl Benzyl Tallow Ammonium

B: Benzyl Dimethyl Coco Ammonium

C: Dihydroxyethyl Benzyl Coco Ammonium

D: Dihydroxyethyl Benzyl Soya Ammonium

E: Benzyl Dimethyl Hydrogenated Tallow Ammonium

This series of tests is conducted in a similar manner to those presented in Examples 1 and 2.

TABLE III

| | ME Ratio to Obtain Zero Microbial Count | |
|---|---|---|
| Test Agent | Amount of Test Agent (% of total cation) | Amount of A (% of total cation) |
| A | 50 | 50 |
| B | 30 | 70 |
| C | 20 | 80 |
| D | 20 | 80 |
| E | 70 | 30 |

Based on the observations made during this study as well as prior evaluation of ammonium cations containing a benzyl group, Table III demonstrates the milliequivalent (ME) ratio of dimethyl dihydrogenated tallow ammonium chloride to the test compounds A, B, C, D and E to achieve essentially zero microbial count using the smallest amount of the test agent.

The invention being thus described, it will be obvious that the same may be varied in many ways. However, such variations are not to be regarded as a departure from the spirit and scope of the invention, and all such modifications are intended to be included within the scope of the following claims.

What is claimed is:

1. A thickened organic topical composition having biocidal activity comprising:
   (a) an organic liquid;
   (b) a first organophilic clay in an amount of from about 0.1 to about 10% by weight of the composition and which will increase the viscosity of the organic liquid, and said first organophilic clay being the reaction product of (i) a smectite-type clay having a cation exchange capacity of at least about 75 milliequivalents per 100 grams of clay, 100% active basis, and (ii) an organic cation having the following formula

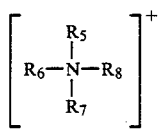

wherein $R_5$ is a linear or branched, saturated or unsaturated alkyl group having 8 to 22 carbon atoms; and $R_6$, $R_7$ and $R_8$ are selected from (a) linear branched alkyl groups having 1 to 22 carbon atoms; (b) aralkyl groups including fused ring moieties having linear or branched 1 to 22 carbon atoms in the alkyl portion of the structure; (c) aryl groups such as phenyl and substituted phenyl including fused ring aromatic substituents; (d) beta, gamma, unsaturated groups having 6 or less carbon atoms or hydroxyalkyl groups having 2 to 6 carbon atoms; and (e) hydrogen, with the proviso that none of $R_6$, $R_7$ or $R_8$ is benzyl; and
   (c) a second organophilic clay in an amount of from about 0.03 to about 3.0% by weight of the composition, which is different from the first organophilic clay and which has biocidal activity, said second organophilic clay being the reaction product of
   (i) a smectite-type clay having a cation exchange capacity of at least about 75 milliequivalents per 100 grams of clay, 100% active basis, and
   (ii) an organic cation having the following formula

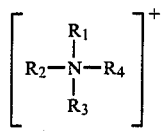

wherein $R_1$ is benzyl; $R_2$ is linear or branched, saturated or unsaturated alkyl group having 8 to 22 carbon atoms; and $R_3$ and $R_4$ are selected from (a) linear or branched alkyl groups having 1 to 22 carbon atoms; (b) aralkyl groups which are benzyl and substituted benzyl moieties including fused ring moieties having linear or branched 1 to 22 carbon atoms in the alkyl portion of the structure; (c) aryl groups such as phenyl and substituted phenyl including fused ring aromatic substituents; (d) beta, gamma, unsaturated groups having 6 or less carbon atoms or hydroxyalkyl groups having 2 to 6 carbon atoms; and (e) hydrogen.

2. The thickened organic topical composition of claim 1 wherein the composition has a microbial count of less than about 10.

3. The thickened organic topical composition of claim 1 wherein the composition is a cosmetic formulation.

4. The thickened organic topical composition of claim 1 wherein the smectite-type clay of the first organophilic clay is selected from hectorite, bentonite and mixtures thereof.

5. The thickened organic topical composition of claim 1 wherein the smectite-clay of the second organophilic clay is selected from hectorite, bentonite and mixtures thereof 6. The thickened organic topical composition of claim 1 wherein the amount of organic cation reacted with the smectite-type clay to form the first and second organophilic clays is from about 90 to about 150% of the exchange capacity of the clay.

7. The thickened organic topical composition of claim 1 wherein in the second organophilic clay $R_2$ is a linear or branched, saturated or unsaturated alkyl group having 12 to 22 carbon atoms and $R_3$ and $R_4$ are lower alkyl containing 1 to 4 carbon atoms or lower hydroxyalkyl containing 2 to 4 carbon atoms.

8. The thickened organic composition of claim 1 wherein in the second organophilic clay $R_2$ is a tallow, coco or soya group.

9. The thickened organic topical composition of claim 1 wherein the organic cation of the second organophilic clay is dimethyl benzyl hydrogenated tallow ammonium.

10. The thickened organic topical composition of claim 1 wherein the organic cation of the second organophilic clay is dihydroxyethyl benzyl coco ammonium chloride.

11. The thickened organic topical composition of claim 1 wherein the organic cation of the second organophilic clay is dihydroxyethyl benzyl tallow ammonium chloride.

12. The thickened organic topical composition of claim 1 wherein the organic cation of the second organophilic clay is dihydroxyethyl benzyl soya ammonium chloride.

13. The thickened organic topical composition of claim 1 wherein the organic cation of the second organophilic clay is dimethyl distilled C-20 alkyl benzyl ammonium chloride.

14. The thickened organic topical composition of claim 1 wherein in the organic cation of the second organophilic clay is dimethyl benzyl coco ammonium chloride.

15. The thickened organic topical composition of claim 1 wherein in the organic cation of the first organophilic clay $R_6$, $R_7$ and $R_8$ are selected from linear or branched alkyl groups having 1 to 22 carbon atoms.

16. The thickened organic composition of claim 15 wherein the organic cation of the first organophilic clay is dimethyl dihydrogenated tallow ammonium.

17. A additive for thickening and imparting biocidal activity to an organic topical composition comprising:
   (a) a first organophilic clay in an amount of from about 50 to about 90% by weight and which will increase the viscosity of the organic composition; and said first organophilic clay being the reaction product of (i) a smectite-type clay having a cation exchange capacity of at least about 75 milliequivalents per 100 grams of clay, 100% active basis, and
   (ii) an organic cation having the following formula

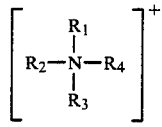

wherein $R_5$ is a linear or branched, saturated or unsaturated alkyl group having 8 to 22 carbon atoms; and $R_6$, $R_7$ and $R_8$ are selected from (a) linear branched alkyl groups having 1 to 22 carbon atoms; (b) aralkyl groups including fused ring moieties having linear or branched 1 to 22 carbon atoms in the alkyl portion of the structure; (c) aryl groups such as phenyl and substituted phenyl including fused ring aromatic substituents; (d) beta, gamma, unsaturated groups having 6 or less carbon atoms or hydroxyalkyl groups having 2 to 6 carbon atoms; and (e) hydrogen, with the proviso that none of $R_6$, $R_7$ or $R_8$ is benzyl; and
   (b) a second organophilic clay in an amount of from about 10 to about 50% by weight, which is different from the first organophilic clay and which has biocidal activity, said second organophilic clay being the reaction product of
   (i) a smectite-type clay having a cation exchange capacity of at least about 75 milliequivalents per 100 grams of clay, 100% active basis, and
   (ii) an organic cation having the following formula

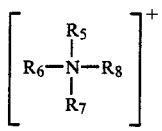

wherein $R_1$ is benzyl; $R_2$ is linear or branched, saturated or unsaturated alkyl group having 8 to 22 carbon atoms; and $R_3$ and $R_4$ are selected from (a) linear or branched alkyl groups having 1 to 22 carbon atoms; (b) aralkyl groups which are benzyl and substituted benzyl moieties including fused ring moieties having linear or branched 1 to 22 carbon atoms in the alkyl portion of the structure;
   (c) aryl groups such as phenyl and substituted phenyl including fused ring aromatic substituents;
   (d) beta, gamma, unsaturated groups having 6 or less carbon atoms or hydroxyalkyl groups having 2 to 6 carbon atoms; and (e) hydrogen.

18. The additive of claim 17 wherein the smectite-type clay of the first organophilic clay is selected from hectorite, bentonite and mixtures thereof.

19. The additive of claim 17 wherein the smectite-type clay of the second organophilic clay is selected from hectorite, bentonite and mixtures thereof.

20. The additive of claim 19 wherein the smectite-type clay is bentonite.

21. The additive of claim 17 wherein the amount of organic cation reacted with the smectite-type clay to form the second organophilic clay is from about 90 to about 150% of the exchange capacity of the clay.

22. The additive of claim 17 wherein the amount of organic cation reacted with the smectite-type clay to form the first organophilic clay is from about 90 to about 150% of the exchange capacity of the clay.

23. The additive of claim 17 wherein the second organophilic clay R2 is a linear or branched, saturated or unsaturated alkyl group having 12 to 22 carbon atoms R3 and R4 are lower alkyl containing 1 to 4 carbon atoms or lower hydroxyalkyl containing 2 to 4 carbon atoms.

24. The additive of claim 23 wherein the second organophilic clay $R_2$ is a tallow, coco or soya group.

25. The additive of claim 17 wherein the organic cation of the second organophilic clay is dimethyl benzyl hydrogenated tallow ammonium.

26. The additive of claim 17 wherein the organic cation of the second organophilic clay is dihydroxyethyl benzyl coco ammonium chloride.

27. The additive of claim 17 wherein the organic cation of the second organophilic clay is dihydroxyethyl benzyl tallow ammonium chloride.

28. The additive of claim 17 wherein the organic cation of the second organophilic clay is dihydroxyethyl benzyl soya ammonium chloride 29. The additive of claim 17 wherein the organic cation of the second organophilic clay is dimethyl distilled C-20 alkyl benzyl ammonium chloride.

30. The additive of claim 17 wherein the organic cation of the second organophilic clay is dimethyl benzyl coco ammonium chloride.

31. The additive of claim 17 wherein the organic cation of the first organophilic clay $R_6$, $R_7$ and $R_8$ are selected from linear or branched alkyl groups having 1 to 22 carbon atoms.

32. The additive of claim 31 wherein the organic cation of the first organophilic clay is dimethyl dihydrogenated tallow ammonium.

33. The additive of claim 17 wherein the first organophilic clay and the second organophilic clay are prepared together and are the reaction product of the smectite-type clay and a mixture of organic cations.

34. A thickened organic topical composition having biocidal activity comprising:
   (a) an organic liquid;
   (b) a first organophilic clay in an amount of from about 0.1 to about 10% by weight of the composition and which will increase the viscosity of the organic liquid; and said first organophilic clay being the reaction product of (i) a smectite-type clay having a cation exchange capacity of at least about 75 milliequivalents per 100 grams of clay, 100% active basis, and (ii) an organic cation having the following formula

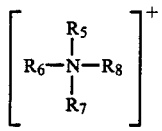

wherein $R_5$ is a linear or branched, saturated or unsaturated alkyl group having 8 to 22 carbon atoms; and $R_6$, $R_7$ and $R_8$ are selected from (a) linear branched alkyl groups having 1 to 22 carbon atoms; (b) aralkyl groups including fused ring moieties having linear or branched 1 to 22 carbon atoms in the alkyl portion of the structure; (c) aryl groups such as phenyl and substituted phenyl including fused ring aromatic substituents; (d) beta, gamma, unsaturated groups having 6 or less carbon atoms or hydroxyalkyl groups having 2 to 6 carbon atoms; and (e) hydrogen, with the proviso that none of $R_6$, $R_7$ or $R_8$ is benzyl; and (c) a second organophilic clay in an amount of from about 0.03 to about 3.0% by weight of the composition, which is different from the first organophilic clay and which has biocidal activity, said second organophilic clay being the reaction product of
(i) a smectite-type clay having a cation exchange capacity of at least about 75 milliequivalents per 100 grams of clay, 100% active basis, and
(ii) an organic cation having the following formula

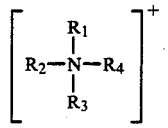

wherein $R_1$ is benzyl; $R_2$ is the amino propyl amide of stearic acid; and $R_3$ and $R_4$ are selected from (a) linear or branched alkyl groups having 1 to 22 carbon atoms; (b) aralkyl groups which are benzyl and substituted benzyl moieties including fused ring moieties having linear or branched 1 to 22 carbon atoms in the alkyl portion of the structure; (c) aryl groups such as phenyl and substituted phenyl including fused ring aromatic substituents; (d) beta, gamma, unsaturated groups having 6 or less carbon atoms or hydroxyalkyl groups having 2 to 6 carbon atoms; and (e) hydrogen.

35. The thickened organic topical composition of claim 34 wherein the organic cation of the second organophilic clay is dimethyl benzyl amino propyl amide of stearic acid ammonium chloride.

36. An additive for thickening and imparting biocidal activity to an organic topical composition comprising:
(a) a first organophilic clay in an amount of from about 50 to about 90% by weight and which will increase the viscosity of the organic composition; and said first organophilic clay being the reaction product of (i) a smectite-type clay having a cation exchange capacity of at least about 75 milliequivalents per 100 grams of clay, 100% active basis, and (ii) an organic cation having the following formula; and

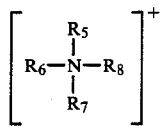

wherein $R_5$ is linear or branched, saturated or unsaturated alkyl group having 8 to 22 carbon atoms; and $R_6$, $R_7$ and $R_8$ are selected from (a) linear or branched alkyl groups having 1 to 22 carbon atoms; (b) aralkyl groups including fused ring moieties having linear or branched 1 to 22 carbon atoms in the alkyl portion of the structure; (c) aryl groups such as phenyl and substituted phenyl including fused ring aromatic substituents; (d) beta, gamma, unsaturated groups having 6 or less carbon atoms or hydroxyalkyl groups having 2 to 6 carbon atoms; and (e) hydrogen, with the proviso that none of $R_6$, $R_7$ or $R_8$ is benzyl less carbon atoms or hydroxyalkyl groups having 2 to 6 carbon atoms; and (e) hydrogen.

37. The additive of claim 36 wherein the organic cation of the second organophilic clay is dimethyl benzyl amino propyl amide of stearic acid ammonium chloride.

* * * * *

UNITED STATES PATENT AND TRADEMARK OFFICE
CERTIFICATE OF CORRECTION

PATENT NO. : 4,929,644

DATED : May 29, 1990  Page 1 of 2

INVENTOR(S) : Ronald D. GUILBEAUX

It is certified that error appears in the above-identified patent and that said Letters Patent is hereby corrected as shown below:

In Claim 1, column 13, line 34, delete "and";
line 48, delete "a";
line 51, before "branched" insert --or--.

In Claim 5 column 14, line 38, after "thereof" insert a period --.--.

In Claim 17, column 15, line 16, amend "A" to --An--;
line 20, amend ";" to --,--;
line 21, delete "and";
line 37, before "branched" insert --or--;

In Claim 23, column 16, line 26, amend "R2" to --$R_2$--;
line 28, amend "R3" and "R4" to --$R_3$-- and --$R_4$--.

In Claim 34, column 16, line 68, amend "; and" to --,--;
column 17, line 13, delete "a";
line 16, before "branched" insert --or--;
line 45, amend "R3" and "R4" to --$R_3$-- and --$R_4$--.

In Claim 36, column 18, lines 16 and 17, amend "; and" to --,--;

UNITED STATES PATENT AND TRADEMARK OFFICE
CERTIFICATE OF CORRECTION

PATENT NO. : 4,929,644

DATED : May 29, 1990

INVENTOR(S) : Ronald D. Guilbeaux

It is certified that error appears in the above-identified patent and that said Letters Patent is hereby corrected as shown below:

lines 21 and 22, delete "; and";

Signed and Sealed this

Twenty-eighth Day of January, 1992

Attest:

HARRY F. MANBECK, JR.

*Attesting Officer*     *Commissioner of Patents and Trademarks*

UNITED STATES PATENT AND TRADEMARK OFFICE
CERTIFICATE OF CORRECTION

PATENT NO. : 4,929,644
DATED      : May 29, 1990
INVENTOR(S) : Ronald D. GUILBEAUX It is certified that error appears in the above-identified patent and that said Letters Patent is hereby corrected as shown below:

In Claim 36, column 18, lines 43-45, amend "less carbon atoms or hydroxyalkyl groups having 2 to 6 carbon atoms; and (e) hydrogen" to -- b) · a second organophilic clay in an amount of from about 10 to about 50% by weight, which is different from the first organophilic clay and which has biocidal activity, said second organophilic clay being the reaction product of
  i) a smectite-type clay having a cation exchange capacity of at least about 75 milliequivalents per 100 grams of clay, 100% active basis, and
  ii) an organic cation having the following formula

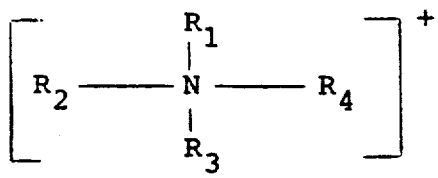

UNITED STATES PATENT AND TRADEMARK OFFICE
CERTIFICATE OF CORRECTION

PATENT NO. : 4,929,644

DATED : May 29, 1990

INVENTOR(S) : Ronald D. GUILBEAUX

It is certified that error appears in the above-identified patent and that said Letters Patent is hereby corrected as shown below:

wherein $R_1$ is benzyl; $R_2$ is the amino propyl amide of stearic acid; and $R_3$ and $R_4$ are selected from (a) linear or branched alkyl groups having 1 to 22 carbon atoms; (b) aralkyl groups which are benzyl and substituted benzyl moieties including fused ring moieties having linear or branched 1 to 22 carbon atoms in the alkyl portion of the structure; (c) aryl groups such as phenyl and substituted phenyl including fused ring aromatic substitutents; (d) beta, gamma, unsaturated groups having 6 or less carbon atoms or hydroxyalkyl groups having 2 to 6 carbon atoms; and (e) hydrogen. --

Signed and Sealed this

Sixteenth Day of March, 1993

Attest:

STEPHEN G. KUNIN

Attesting Officer

Acting Commissioner of Patents and Trademarks